US010219981B2

(12) United States Patent
Ludin et al.

(10) Patent No.: US 10,219,981 B2
(45) Date of Patent: Mar. 5, 2019

(54) FLUID CONTAINERS AND SYSTEMS AND METHODS FOR DETECTING A FLUID LEVEL THEREIN

(71) Applicant: INTEGRA LIFESCIENCES SWITZERLAND SÀRL, Le Locle (CH)

(72) Inventors: Lev Ludin, Newton, MA (US); Michael A. DeFusco, North Attleboro, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 0 days.

(21) Appl. No.: 15/476,202

(22) Filed: Mar. 31, 2017

(65) Prior Publication Data

US 2018/0280236 A1 Oct. 4, 2018

(51) Int. Cl.
 *G06K 19/00* (2006.01)
 *A61J 1/18* (2006.01)
 (Continued)

(52) U.S. Cl.
 CPC .............. *A61J 1/18* (2013.01); *A61M 1/0001* (2013.01); *A61M 1/0019* (2013.01); *A61M 27/006* (2013.01); *G01F 23/242* (2013.01); *G01F 23/243* (2013.01); *G06K 7/10366* (2013.01); *G06K 19/07773* (2013.01); *G06K 19/07779* (2013.01); *A61B 5/208* (2013.01); *A61F 5/44* (2013.01); *A61J 2200/76* (2013.01);
 (Continued)

(58) Field of Classification Search
 USPC .......................... 235/435, 439, 454, 487, 492
 See application file for complete search history.

(56) References Cited

U.S. PATENT DOCUMENTS 4,433,577 A 2/1984 Khurgin et al.
5,098,409 A 3/1992 Stock
(Continued)

FOREIGN PATENT DOCUMENTS

WO 2016/166338 A1 10/2016

OTHER PUBLICATIONS

The PCT Search Report and Written Opinion of the PCT Application Serial No. PCT/IB2018/052271, dated Aug. 28, 2018 (42 pages).

*Primary Examiner* — Matthew Mikels
(74) *Attorney, Agent, or Firm* — Troutman Sanders LLP

(57) ABSTRACT

Fluid containers having a volume marking(s) and conductive element(s) disposed at the volume marking(s) and a common conductive element are provided. For example, the fluid container has a wall forming the volume. The conductive element(s) and the common conductive element have a portion disposed within the volume and a portion external to the volume. The container further has a RFID tag, where the conductive element(s) and the common conductive element are connected thereto via respective conductive wires. A fluid detection system having the fluid containers is also provided. The system comprises one or more containers and a patient site monitor having a RF reader that interrogates the RFID tag at a preset interval. Responsive to the signal, the tag supplies a predetermined current to the conductive element and the common conductive element and detects a voltage and generates an alert based on the same.

21 Claims, 6 Drawing Sheets

(51) Int. Cl.
  *A61M 27/00* (2006.01)
  *G06K 7/10* (2006.01)
  *G06K 19/077* (2006.01)
  *A61M 1/00* (2006.01)
  *G01F 23/24* (2006.01)
  *A61M 5/168* (2006.01)
  *A61B 5/20* (2006.01)
  *A61F 5/44* (2006.01)

(52) U.S. Cl.
  CPC .......... *A61J 2205/60* (2013.01); *A61M 5/168* (2013.01); *A61M 5/1684* (2013.01); *A61M 2205/3317* (2013.01); *A61M 2205/3389* (2013.01); *A61M 2205/3561* (2013.01); *A61M 2205/3592* (2013.01)

(56) References Cited

U.S. PATENT DOCUMENTS

| | | |
|---|---|---|
| 5,135,485 A | 8/1992 | Cohen et al. |
| 7,049,969 B2 | 5/2006 | Tamai |
| 7,976,508 B2 | 7/2011 | Hoag |
| 7,982,612 B2 | 7/2011 | Braun |
| 8,736,455 B2 | 5/2014 | Linsenmeyer et al. |
| 8,869,612 B2 | 10/2014 | Chen et al. |
| 2008/0051937 A1 | 2/2008 | Khan et al. |
| 2009/0088710 A1 | 4/2009 | Hoffman et al. |
| 2011/0174067 A1 | 7/2011 | Boiarski |
| 2011/0304468 A1 | 12/2011 | Linsenmeyer et al. |
| 2012/0109008 A1* | 5/2012 | Charlez .............. A61B 5/14507 600/573 |
| 2012/0302938 A1 | 11/2012 | Browd et al. |
| 2012/0319852 A1 | 12/2012 | Platten et al. |
| 2013/0030262 A1 | 1/2013 | Burnett et al. |
| 2014/0278156 A1 | 9/2014 | Thompson et al. |
| 2015/0033847 A1 | 2/2015 | Chen et al. |
| 2015/0112289 A1 | 4/2015 | Stebbins et al. |
| 2015/0362351 A1 | 12/2015 | Joshi et al. |
| 2016/0310711 A1 | 10/2016 | Luxon et al. |
| 2016/0320222 A1* | 11/2016 | Dulaff ................... G01F 23/265 |
| 2017/0020724 A1 | 1/2017 | Burnett et al. |

\* cited by examiner

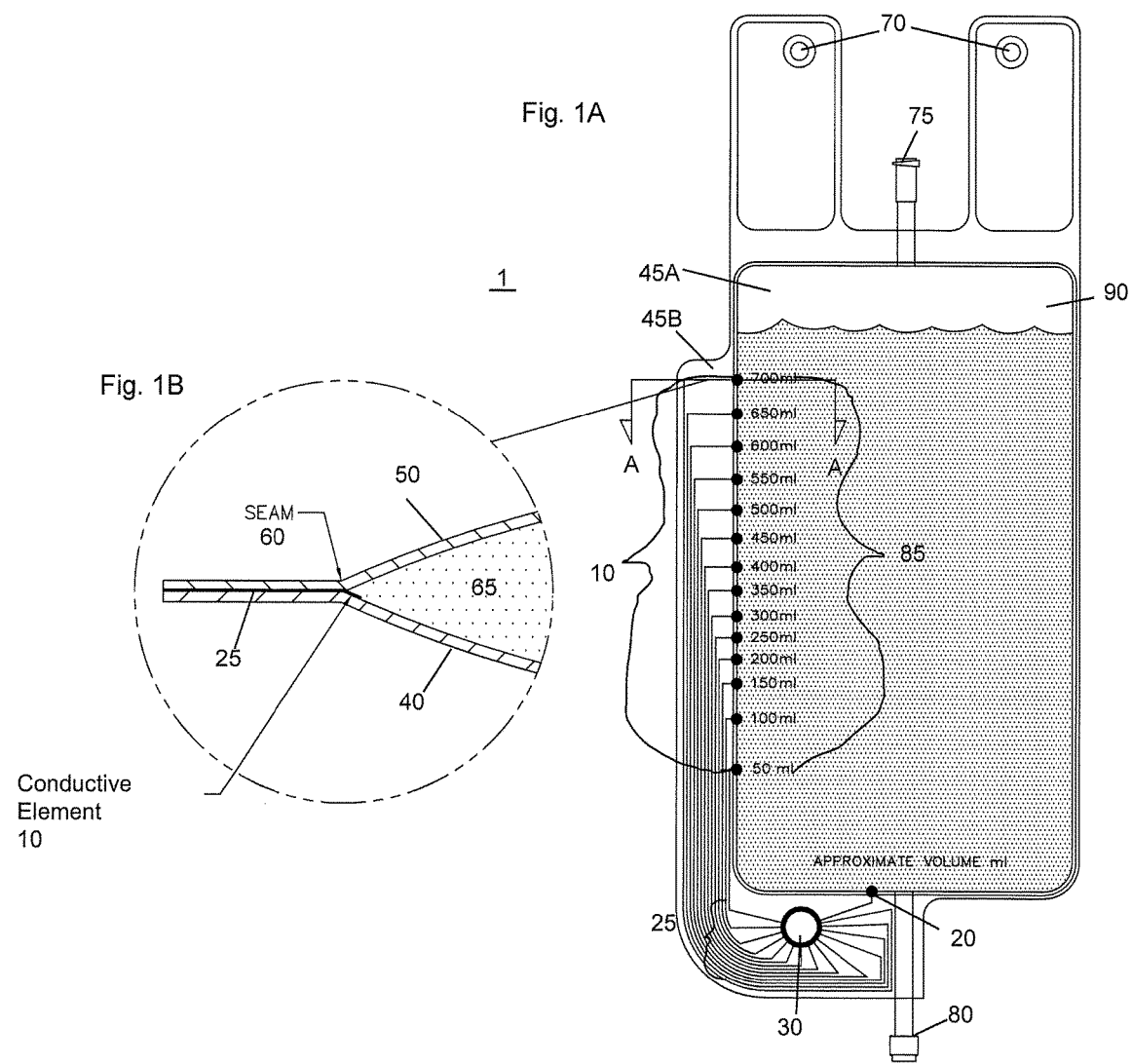

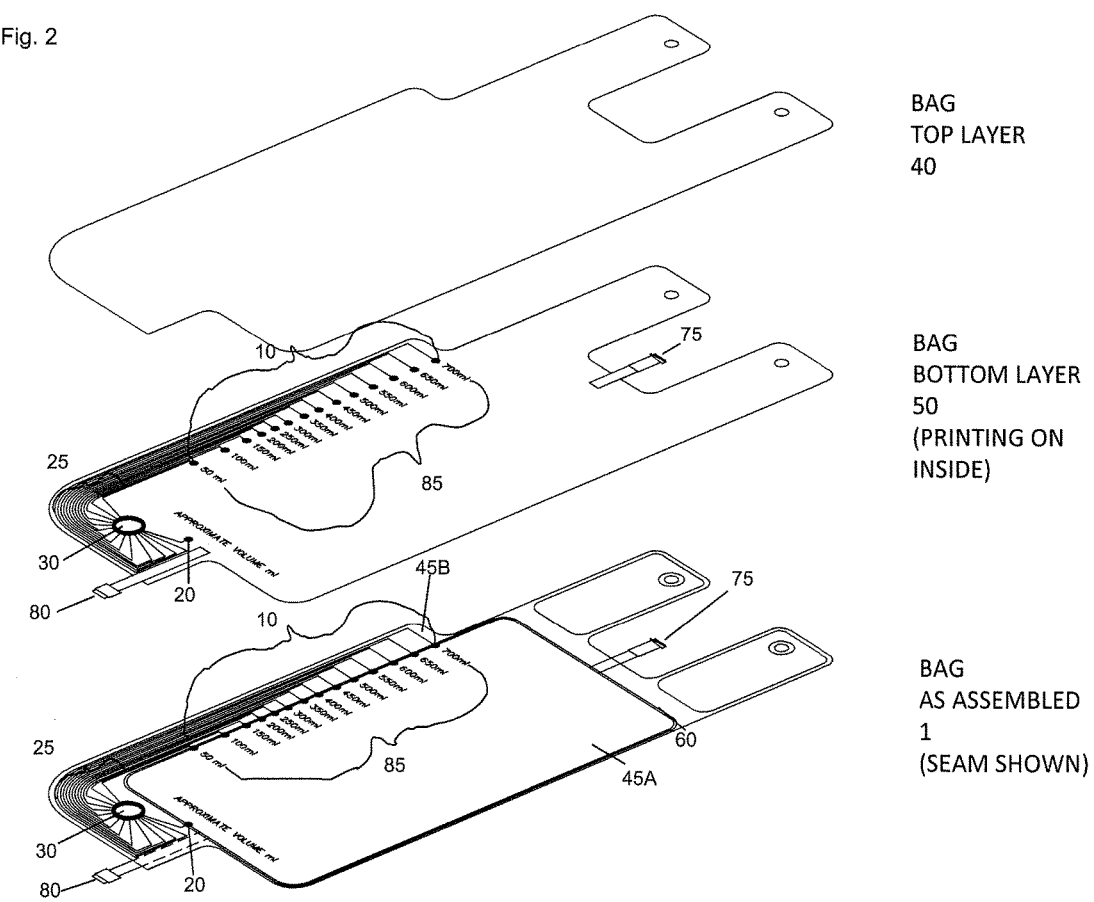

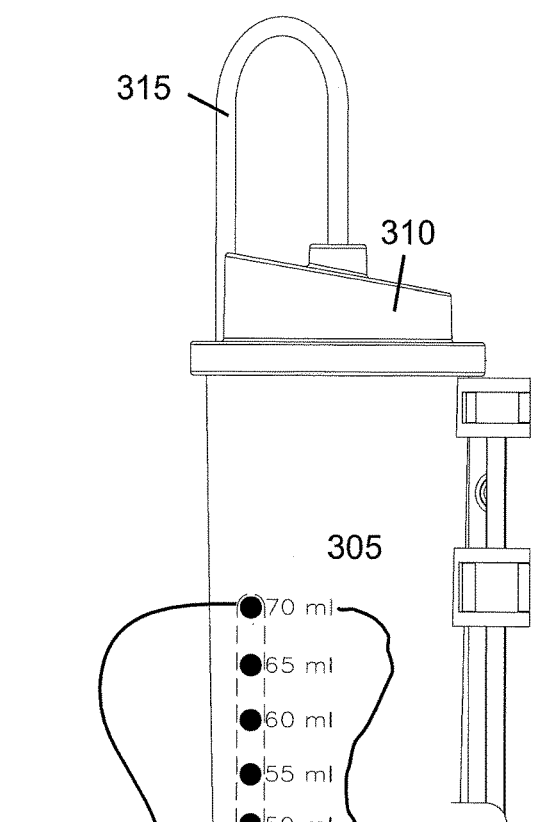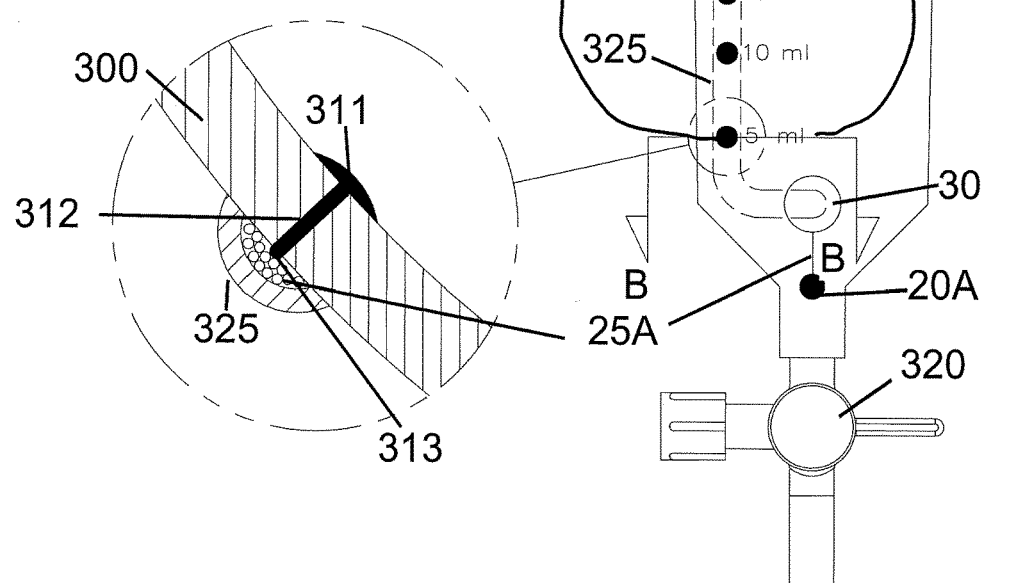

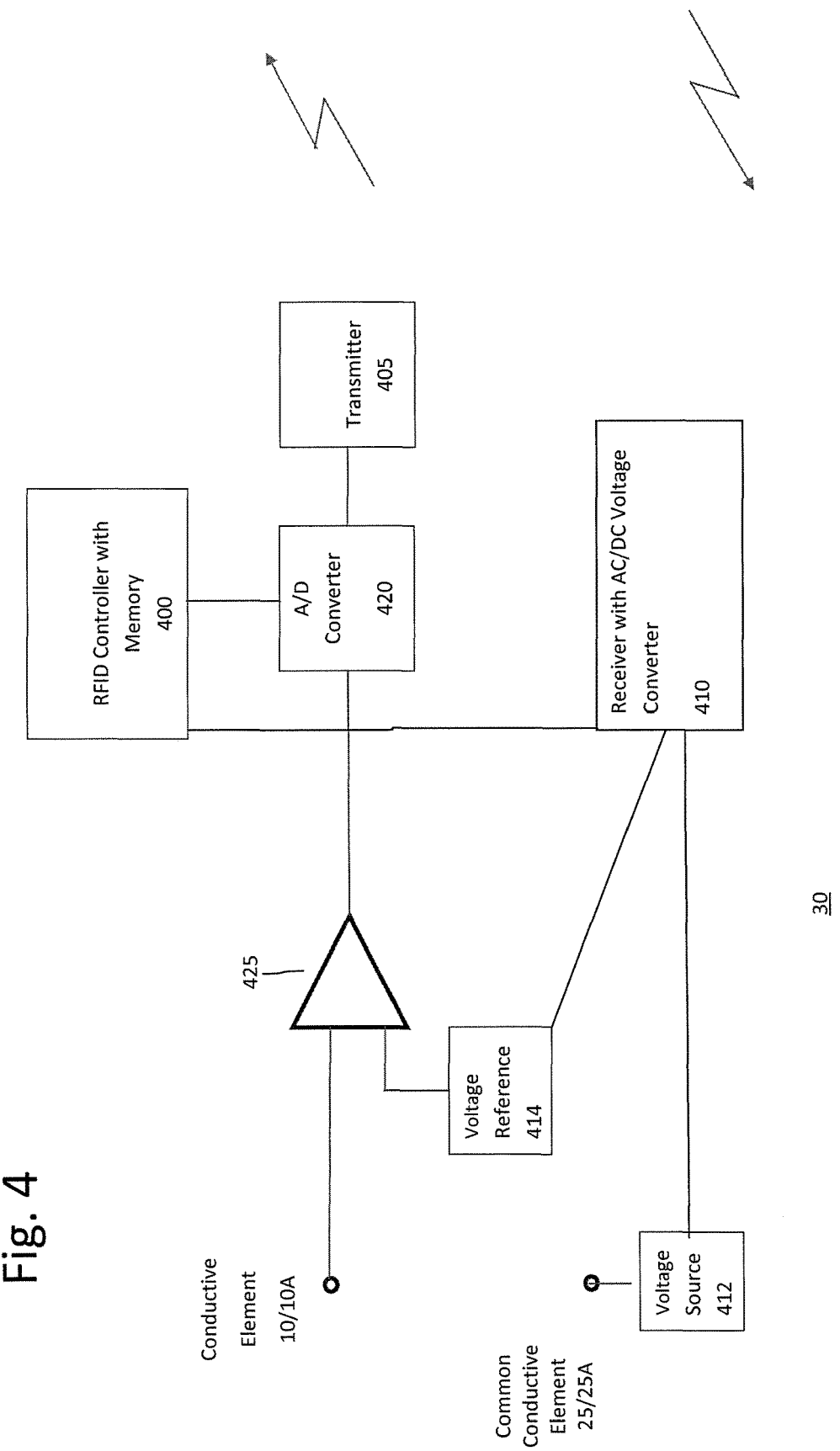

FLUID CONTAINERS AND SYSTEMS AND METHODS FOR DETECTING A FLUID LEVEL THEREIN

FIELD OF THE DISCLOSURE

This disclosure relates to fluid containers. This disclosure also relates to systems and methods for detecting the fluid level in fluid containers.

BACKGROUND

Fluid containers can hold various types of fluids. For example, in medical applications certain body fluids can be drained into a fluid container. The body fluids can be, but are not limited to, blood, urine and intracranial fluid. Further, fluid containers can be used for saline solutions and medicine.

Fluid containers can be flexible such as an IV or drainage bag or rigid such as a burette. The fluid container can be flow regulated such as a graduated drip chamber.

In medical applications, it is important to track the fluid level or fluid volume in the fluid container. For example, a healthcare provider needs to know when the fluid container is full and/or needs to be replaced. Additionally, if medicine or saline is used, it is equally important to know when the fluid container is empty.

SUMMARY OF THE DISCLOSURE

Disclosed is a fluid container comprising a wall forming a volume for holding a fluid. The wall has a volume marking indicating a volume level. The fluid container further comprises a conductive element disposed at the volume level, a RFID tag and a common conductive element. The conductive element has a portion disposed within the volume and a portion external to the volume. The common conductive element has a portion disposed within the volume and a portion external to the volume. Both the common conductive element and the conductive element are connected to the RFID tag via a respective conductive wire.

Also disclosed is a fluid detection system. The fluid detection system comprises a fluid container and a patient site monitor having a RF reader. The fluid container has a wall, where at least a portion of the wall defines a volume to hold a fluid. The wall has a volume marking indicating a volume level. A RFID tag is attached to the wall of the fluid container. The fluid container further comprises a conductive element disposed at the volume level and a common conductive element. The conductive element has a portion disposed within the volume and a portion external to the volume and the common conductive element has a portion disposed within the volume and a portion external to the volume. The common conductive element and the conductive element are connected to the RFID tag via respective conductive wires.

The RF reader of the patient site monitor is configured to interrogate the RFID tag at a preset interval by transmitting a signal. When the RFID tag receives the signal, the RFID tag supplies a predetermined current to the conductive element and the common conductive element and detects a voltage. The RFID tag is configured to generate an alert based on the voltage responsive to the signal.

BRIEF DESCRIPTION OF THE FIGURES

FIG. 1A illustrates a plan view of a fluid container in accordance with aspects of the disclosure;

FIG. 1B illustrates a sectional view along the A-A line;

FIG. 2 illustrates an isometric view of the fluid container in accordance with aspects of the disclosure;

FIG. 3A illustrates a plan view of another fluid container in accordance with aspects of the disclosure;

FIG. 3B illustrates a sectional view along the B-B line;

FIG. 4 illustrates a schematic diagram of an RFID tag for a fluid container in accordance with aspects of the disclosure;

DETAILED DESCRIPTION

Figure 5:
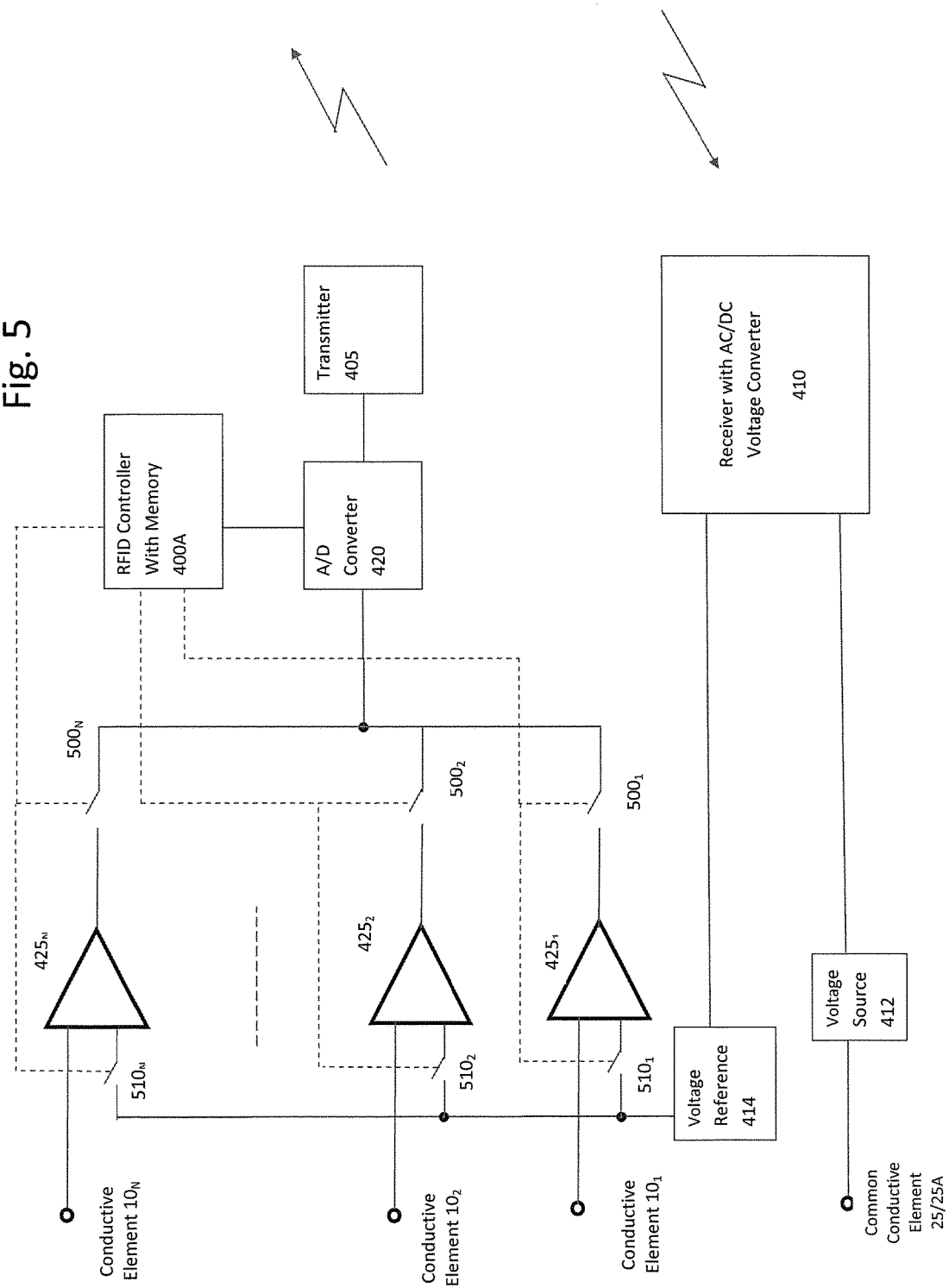
FIG. 5 illustrates a schematic diagram of another RFID tag for a fluid container in accordance with aspects of the disclosure.

FIG. 1A depicts a fluid container in accordance with aspects of the disclosure. The fluid container depicted in FIG. 1A is flexible. The fluid container depicted in FIG. 1A will also be called a fluid collection bag 1 herein. The fluid collection bag 1 can be a bag for use as an IV. Further, the fluid collection bag 1 can hold blood, urine, intracranial fluids, saline solutions or other medicine, as needed.

The fluid collection bag 1 includes a pocket or main body 90 defining a fluid volume or space which holds fluid. The pocket or main body 90 is formed from walls or layers 40, 50. For purposes of the description, wall 40 will be referred to as "front wall" and wall 50 will be referred to as "rear wall", however, the reference to "front" and "rear" is not defining a use orientation.

The walls 40, 50 can be made from one or more of plastic materials such as a thermoplastic material, polyvinyl chloride (PVC) or other films such as ethylene vinyl acetate (EVA). The walls 40, 50 are sealed together to form the pocket or main body 90. The walls 40, 50 can be sealed together using a heat sealing method to form a seam 60. The seam 60 surrounds the pocket or main body 90.

As depicted, each of the front wall 40 and rear wall 50 has two portions. A first portion 45A that when fluid is in the fluid collection bag can be exposed to the fluid and a second portion 45B, that even when fluid is in the fluid collection bag 1 will not be exposed to the fluid. The seam 60 acts as a boundary between the first portion 45A and the second portion 45B.

One of the walls of the fluid collection bag 1 includes volume markings 85. As depicted, the volume markings 85 start from 50 ml and end with 700 ml and are listed in increments of 50 ml. However, the markings depicted in the figures are examples for descriptive purposes and the markings are not limited thereto. The specific amount of fluid that the fluid collection bag 1 can hold and the markings can vary, as needed. FIG. 2 shows the volume markings 85 on the rear wall or layer 50, however, the markings are not limited thereto and can be on the front wall or layer 40. Also as depicted, the volume markings 85 are aligned adjacent to the seam 60, however, the markings are not limited to these positions.

Conductive elements 10 are vertically aligned along the seam 60. The conductive element can be a conductive paint or ink or a conductive wire. The conductive elements 10 are disposed at predetermined volume levels. As depicted in FIG. 1A, the conductive elements 10 are disposed adjacent to the volume markings 85 and disposed at 50 ml increments. Similar to the volume markings 85, the position of the conductive elements 10 are not limited to the depicted increments and can be disposed as needed at certain volume levels. For example, a single conductive element can be placed as a maximum fill level.

The conductive elements 10 are positioned along the seam 60 such that when the walls 40 and 50 are sealed, a portion of the conductive element is exposed to the volume 90 and a portion of the conductive element is not exposed. For example, FIG. 1B shows a sectional view of the fluid collection bag 1. As can be seen in FIG. 1B, a portion of the conductive element 10 is in contact with the fluid 65.

As depicted in the FIG. 1A, the conductive elements are shown as circles, where part is in the first portion 45A and part is in the second portion 45B. It is noted that the depiction of the conductive element as a circle is for descriptive purposes only to distinguish between conductive wires 25.

The fluid collection bag 1 further includes a RFID tag 30. The RFID tag 30 will be described in detail later. The RFID tag 30 is disposed between the front and rear walls 40, 50. Additionally, the RFID tag 30 is disposed within the second portion 45B of the walls such that the RFID tag 30 is not exposed to fluid. Thus, the RFID tag 30 is disposed between the heat sealed front and rear walls 40, 50.

The conductive elements 10 are connected to the RFID tag 30 via conductive wires 25. The conductive elements 10 can be a separate element from the conductive wires or integral. For example, when a conductive paint or ink is used as the conductive element, the same conductive ink can be used as the conductive wire 25.

The fluid collection bag 1 further includes a common conductive element 20. Similar to the conductive elements 10, the common conductive element 20 is disposed along the seam 60 such that a portion of the common conductive element 20 is within the pocket or main body 90 and within the first portion 45A and a portion of the common conductive element 20 is not exposed to the fluid and is located within the second portion 45B. The common conductive element 20 is disposed on the bottom of the pocket or main body 90.

Thus, a portion of both the common conductive element 20 and a portion of the conductive element 10 are disposed between the heat sealed front and rear walls 40, 50

The common conductive element 20 is connected to the RFID tag 30 via one of the conductive wires 25. The common conductive element 20 can be a separate element from the conductive wire or integral. For example, when a conductive paint or ink is used as the common conductive element 20, the same conductive ink can be used for its conductive wire 25. Thus, each conductive wire 25 is disposed between the heat sealed front and rear walls 40, 50.

FIG. 2 illustrates an isometric view of the fluid collection bag 1. As shown, the conductive elements 10, common conductive element 20 and conductive wires 25 are printed on the inside of the rear wall 50. Alternatively, the conductive elements 10, common conductive element 20 and conductive wires 25 can be printed on the inside of the front wall 40.

The conductive wires 25 are positioned entirely within the second portion 45B such that the wires 25 are not exposed to the fluid 65. Similarly, as shown in FIG. 2, the RFID tag 30 is also disposed entirely within the second portion 45B. As assembled, the conductive elements 10, common conductive element 20 and conductive wires 25 and RFID tag 30 are sealed between the front wall 40 and rear wall 50 (as shown in the assembled view).

The fluid collection bag 1 also has fluid ports 75, 80, one at the top of the pocket or main body 90 and one at the bottom of the pocket or main body 90. Once again, the use of "top" and "bottom" is for descriptive purposes only and not necessarily reflective of a use orientation.

The fluid ports 75, 80 are for either filling the fluid collection bag 1 or draining the same. The fluid ports 75, 80 are adapted to be connectible with fluid supply lines. The ports 75, 80 are sealed between the front wall 40 and back wall 50 and have an opening in fluid communication with the pocket or main body 90.

The fluid collection bag 1 has openings 70 such that the bag can be hung on a bar or pole.

FIG. 3A depicts another fluid container in accordance with aspects of the disclosure. The fluid container depicted in FIG. 3A can be rigid and not flexible. The fluid container depicted in FIG. 3A will also be called a burette 1A herein.

The burette 1A has a wall 300 and a cap 310. The wall 300 is cylindrical in shape and tapered at the bottom. The wall 300 defines a volume or space 305 for a fluid. The cap 310 covers the top of the wall 300. The cap 310 has an opening adapted to engage with a fluid supply line 315. The burette 1A further has a drip valve 320 configured to control the flow of fluid draining from the burette 1A.

The wall 300 of the burette 1A includes volume markings 85. As depicted, the volume markings 85 start from 5 ml and end with 70 ml and are listed in increments of 5 ml. However, the volume markings 85 depicted in the figures are examples for descriptive purposes and the markings are not limited thereto. The specific amount of fluid that the burette 1A can hold and the volume markings can vary, as needed.

Conductive elements 10A are vertically aligned. Each conductive element can be a conductive pin. The conductive elements 10A are disposed at predetermined volume levels. As depicted in FIG. 3A, the conductive elements 10A are disposed adjacent to the volume markings 85 and disposed at 5 ml increments. Similar to the volume markings 85, the position of the conductive elements 10A is not limited to the depicted increments and can be disposed as needed as certain volume levels. For example, a single conductive element can be placed as a maximum fill level.

Each conductive pin has a portion disposed within the volume or space 305 (referred to as the pin head 311). Each conductive pin extends through the wall 300 having its body 312 embedded in the wall 300. A portion of the conductive pin is external to the wall 300 (referred to as the tip 313) as shown in FIG. 3B (which is sectional view along the B-B line). The pin head 311 is attached to the interior surface of the wall and creates a seal such that the fluid cannot escape through the pin holes in the wall. For example, the pin head 311 can be glued to the interior wall with epoxy.

Since the pin head 311 is within the volume or space 305, when fluid is within the space, the fluid is capable of contacting the pin head 311.

The burette 1A further includes a RFID tag 30. The RFIG tag 30 will be described in detail later. The RFID tag 30 is disposed on the exterior surface of the wall 300.

As depicted in FIG. 3A, the RFID tag 30 is located near the bottom of the burette 1A. However, the location of the RFID tag 30 is not limited to the depicted position.

The conductive elements 10A, e.g., pins, are connected to the RFID tag 30 via conductive wires 25A. Each pin is electrically coupled to a separate conductive wire. A sectional view of the conductive wires 25A is shown in FIG. 3B. The conductive wires 25A have an insulating material on the outside. The insulating material is removed at the position where the wire is connected with the tip 313 of the conductive pin. Since the conductive elements 10A are located at different vertical positions, the lengths of each conductive wire are different. FIG. 3A depicts the conductive elements 10A being vertically aligned. However, the conductive elements 10A do not have to be vertically aligned, but rather can be offset.

The burette 1A further includes a common conductive element 20A. Similar to the conductive elements 10A, the common conductive element 20 can be a conductive pin, with the pin head 311 being disposed within the pocket or main body 305 and attached to the interior surface of the wall 300. The body of the pin 312 is embedded within the wall and the tip 313 of the pin is external to the wall.

The common conductive element 20A is connected to the RFID tag 30 via one of the conductive wires 25A.

A cover 325 covers and protects the conductive elements 10A and conductive wires 25A. The cover 325 can be made from the same material as the burette 1A. Alternatively, the cover 325 can be a flexible material such as tape.

The burette 1A can also have a separate cover covering the common conductive element 20A and the conductive wire which connects the common conductive element 20A and the RFID tag.

FIG. 4 is a schematic diagram of an RFID tag 30 in accordance with aspects of the disclosure. The RFID tag 30 can be used for both the fluid collection bag 1 and the burette 1A. This RFID tag 30 can be used when the fluid collection device includes one conductive element 25/25A or one level of fluid is monitored.

In an aspect of the disclosure, the RFID tag 30 is a passive tag. As such, the RFID tag 30 does not include a separate battery for supplying power thereto, but rather uses energy from a received RF signal to power the components. Alternatively, the RFID tag 30 can be an active tag with an onboard battery.

The RFID tag 30 comprises a RFID controller with Memory 400. The RFID controller 400 is configured to control the RFID tag 30 and maintain clock timing. The memory is capable of storing instructions for the RFID controller 400 as well as detected fluid level(s) for a given period. The RFID tag 30 further comprises a transmitter for transmitting signals to a RF Reader in a Patient Monitor.

The RFID tag 30 further comprises a Receiver with an AC/DC Voltage Converter 410. As noted above, the RFID tag 30 is a passive tag and the power is generated from the received RF signal via the AC/DC Voltage Converter. The AC/DC Voltage Converter is electrically coupled with the RFID Controller 400 and also with the conductive element 10/10A and common conductive element 25/25A. Thus, the AC/DC Voltage Converter can supply a predetermined voltage (or current) to the conductive element 10/10A and common conductive element 25/25A. Additionally, the AC/DC Voltage Converter can supply a reference value for comparison (e.g., Voltage Reference 414).

The RFID tag 30 further comprises a comparator 425 for comparing values from the conductive element 10/10A and the reference. The voltage source 412 (or current) and voltage reference (or current) can be set to a predetermined value using a resistor(s) respectively connected between the AC/DC Converter and conductive element 10/10A and common conductive element 25/25A and also the comparator 425. One terminal of the comparator 425 is coupled to the conductive element 10/10A and the other is coupled to a reference. The comparator 425 effectively determines a change in impedance in the conductive element 10/10A as a result of being in contact with the fluid.

The RFID tag 30 further comprises an A/D Converter 420. The A/D Converter 420 is connected to the RFID Controller 400 and the output of the comparator 425. The A/D Converter based on the result of the output, generates a signal for transmission by the transmitter 405, e.g., an alert.

The RFID tag 30 further comprises a Transmitter 405. The Transmitter 405, such as a coil, is coupled to the A/D Converter 420. The transmitter 405, responsive to the RFID tag 30 receiving a signal from a RF Reader, is configured to transmit a response. Depending on the results of the comparison, the transmitter 405 is configured to transmit an alert as the response.

FIG. 5 illustrates a schematic diagram of an RFID tag 30A in accordance with another aspect of the disclosure. The RFID tag 30A is used for a fluid container that has a plurality of conductive elements $10/10A_{1-N}$. A difference between the RFID tag 30 and RFID tag 30A is that RFID tag comprise a plurality of comparators 425 and switches 500. The RFID Controller 400A can sequentially control the switches 500 to selectively couple (open or close) the output of a respective comparator to the RFID Controller 400A and then to the A/D Converter 420.

The conductive elements 10/10A are respectively coupled to one of the terminals of the comparator 425. In FIG. 4, for description purposes only the conductive elements are labeled $10_1$-$10_N$. However, the conductive elements can also be $10A_1$-$10A_N$. For example, conductive element $10_1$ ($10A_1$) is coupled to one of the terminals of comparator $425_1$ and conductive element $10_N$ ($10A_N$) is coupled to one of the terminals of comparator $425_N$.

Each switch 500 in individually controlled by the RFID Controller 400A to sequentially couple the respective outputs of the comparators 425 to the RFID Controller 400A.

In an aspect of the disclosure, the reference value for each of the comparators 425 can be the same. Alternatively, in another aspect of the disclosure, the reference value for each comparator 425 can be different. The reference value for a comparator is set using a specific resistance value for a resistor(s). Thus, where there are different reference values, a different resistor or a different number of resistors can be coupled to a terminal of a respective comparator 425.

Each comparator 425 effectively determines a change in impedance in the conductive element $10_{1-N}$ ($10A_{1-N}$) as a result of being in contact with the fluid.

Figure 6:
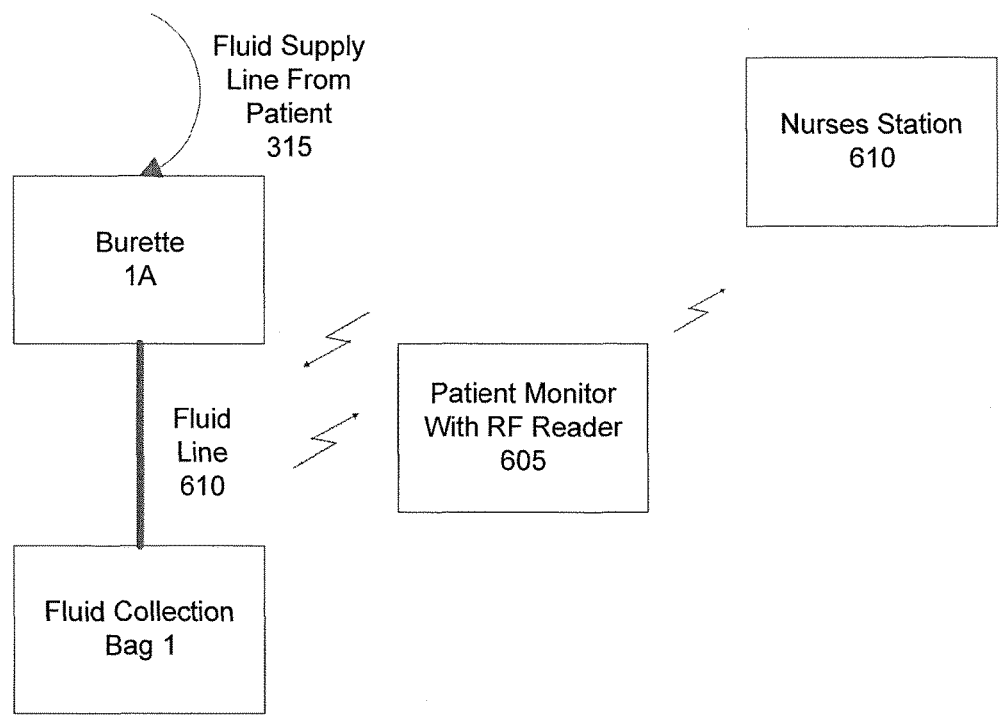
FIG. 6 illustrates a system for detecting a fluid volume in fluid containers in accordance with aspects of the disclosure.

FIG. 6 illustrates a system 600 for detecting a fluid volume in one or more fluid containers having the above described design.

In accordance with aspects of the disclosure, an RF Reader is co-located within a Patient Monitor 605. For example, a wireless adaptor can be installed into a patient monitor. The RF Reader is configured to periodically poll the RFID tags 30/30A in the fluid containers. In an aspect of the disclosure, if there are more than one RFID tags 30/30A in radio distance of the RF Reader, the RF Reader can sequentially poll each tag such that only one RFID tag 30/30A responds at a given time. Alternatively, in an aspect of the disclosure, the RF Reader is configured to transmit a different frequency to each fluid container within the radio distance. As depicted in FIG. 6, the system 600 includes two fluid containers: a fluid collection bag 1 and a burette 1A.

The burette 1A is connected to the fluid collection bag 1 via a fluid line 610. The fluid line 610 is connected to port 75 of the fluid collection bag 1. A fluid supply line 315 is connected to the cap 310 of the burette 1A. For example, the fluid supply line 315 can be a catheter, such as an intracranial catheter.

For instance, the RF Reader in the Patient Monitor 605 can first poll the RFID tag 30/30A in the fluid Collection Bag 1. As noted above, the RFID tag 30/30A is a passive tag. The following description is for the operation of the RFID tag 30

(where there is either one conductive element or one monitored level) in response to the polling signal from the RF Reader.

The RFID tag 30 receives the polling signal from the RF reader at receiver 410. The AC/DC Voltage Converter generates the power for the RFID tag 30 from the energy in the RF signal. Specifically, the AC/DC Voltage Converter supplies a DC voltage to the Voltage Source 412. In an aspect of the disclosure, the Voltage Source 412 in turn supplies either a predetermined DC voltage (or a predetermined DC current to the common conductive element 25 and the conductive element 10.

A resultant voltage or current is seen at one of the terminals of the comparator 425. Additionally, AC/DC Voltage Converter supplies a DC voltage to the Voltage Reference 414. The voltage reference is set to a value equal to a value where the conductive element 10 is not in contact with the fluid. A resultant voltage or current from the voltage reference (current reference) is seen at the other of the terminals of the comparator 425. The comparator 425 compares the values of the voltages (or currents). If the voltages (or currents) are the same, it indicates that the conductive element 10 is not in contact with the fluid. On the other hand, if the voltage (or current) is different, such as being greater, it indicates that the conductive element 10 is in contact with the fluid and thus, the fluid level is at or above the volume level associated with the conductive element 10.

In an aspect of the disclosure, the RFID Controller 400 receives the output of the comparator 425. If the output indicates that the voltage (or current) is different, the RFID Controller 400 causes the A/D converter 420 to convert the output of the comparator into a signal for transmission and causes the transmitter 405 to transmit an alert to the Patient Monitor 605. The alert can include an identifier of the RFID tag 30. In another aspect of the disclosure, instead of converting the output of the comparator into a signal for transmission (such as a digital signal), a preset signal for the alert can be used (converted and transmitted).

In another aspect of the disclosure, instead of transmitting an alert upon a first instance of the voltage (or current) being determined to be different from the reference value, an alert can be transmitted when at least a certain number of polling periods have occurred when the voltage (or current) is different. For example, the memory of the RFID Controller can store at least one previous result of the comparison and a transmission threshold. If the transmission threshold is two polling periods, the RFID Controller 400 can cause the alert to be generated when the voltage (or current) is determined to be different for two consecutive polling periods. Thus, the RFID Controller 400 can retrieve a previous determination from memory and examine the transmission threshold and compare the previous determination(s) with a current determination.

In another aspect of the disclosure, instead of transmitting an alert upon a first instance of the voltage (or current) being determined to be different from the reference value, an alert can be transmitted based on looking at the difference between the values (voltage or current) from consecutive polling periods, e.g., the delta, without using a separate reference value. A change in the values (voltage or current) indicates that the fluid level has reached the conductive element (whereas the period prior it did not). For example, a value from a previous polling period is supplied to one terminal of the comparator and a value from the current polling period is supplied to the other terminal.

In another aspect of the disclosure, instead of the RFID controller 400 determining whether an alert should be transmitted based on the output of the comparator 425, the A/D converter 420 converts the output of the comparator 425, for each instance of the polling, and the raw data is transmitted by the transmitter 405 for external evaluation.

In other aspects of the disclosure, one or more of the above described ways are combined for confirmation of the initial determination of the fluid level or volume.

If the Patient Monitor 605 receives an alert from the RFID tag 30 (via the RF reader), the Patient Monitor 605 sends an alert to the nurses station 610. The nurses station 610 can include a display and the alert can be displayed on the display. Additionally and/or alternatively, the nurses station 610 can include a speaker and an audible alert can be generated. In response to the alert, a nurse can change the fluid collection bag 1, if needed. Furthermore, the nurse can record the fluid level in a patient's file.

The patient monitor 605 will also poll the burette 1A having the RFID tag 30. The RFID tag 30 in the burette responds in the same way as described above and will not be described again in detail.

The following description is for the operation of the RFID tag 30A in response to the polling signal from the RF Reader.

The RFID tag 30A receives the polling signal from the RF reader at receiver 410. The AC/DC Voltage Converter generates the power for the RFID tag 30A from the energy in the RF signal. Specifically, the AC/DC Voltage Converter supplies a DC voltage to the Voltage Source 412. In an aspect of the disclosure, the Voltage Source 412 in turn supplies either a predetermined DC voltage (or a predetermined DC current) to the common conductive element 25A and the conductive elements 10A.

Resultant voltages or currents are respectively seen at one of the terminal of each comparator $425_{1-N}$. Additionally, AC/DC Voltage Converter supplies a DC voltage to the Voltage Reference 414. The voltage reference is set to a value equal to a value where each conductive element is not in contact with the fluid. A resultant voltage or current from the voltage reference (current reference) is seen at the other of the terminals of each comparator $425_{1-N}$.

Each comparator 425 is associated with a specific volume level. For example, comparator $425_1$ can be associated with level 50 ml (as shown in FIG. 1A), comparator $425_2$ can be associated with level 100 ml . . . comparator $425_N$ can be associated with 700 ml.

Each comparator 425 compares the values of the voltages (or currents), e.g., from the respective conductive element and respective reference value. If the voltages (or currents) are the same, it indicates that the associated conductive element 10A is not in contact with the fluid 65. On the other hand, if the voltage (or current) is different, such as being greater, it indicates that a conductive element 10A is in contact with the fluid 65 and thus, the fluid level is at or above the volume level associated with the conductive element 10A.

The RFID Controller 400A sequentially controls the switches 500 to close (and open) to selectively couple the output of the comparator to the RFID Controller 400A and A/D Converter.

In another aspect of the disclosure, the RFID tag 30A includes a second set of switches $510_N$ configured to selectively couple the voltage or current to each of the conductive elements and/or the reference sequentially. As shown in FIG. 5, the switches 510 are connected to the reference terminal of the comparator, however, in another aspect of the disclosure, the switches can be connected to the other terminal or to both terminals. The RFID Controller 400A closes the sets of switches (500 and 510) for the same conductive element and comparator at the same time and sequences the switching such that switches corresponding to the same conductive element and comparator are also closed/opened at the same time.

Consistent with the operation of the switches 500, 510, the RFID Controller 400A selectively receives the output of each comparator 425 in sequence. If the output indicates that the voltage (or current) is different from its respective reference, the RFID Controller 400A determines which comparator outputted the signal. In an aspect of the disclosure, the memory in the RFID Controller 400A includes a set volume for the transmission of an alert. This set volume is associated with a given comparator. For example, the set volume can be 500 ml which is associated with comparator $425_{10}$. The RFID Controller 400A will cause the A/D converter 420 to convert the output of the comparator into a digital signal if comparator $425_{10}$ (or a comparator associated with a volume above the same) indicated a difference and cause the transmitter 405 to transmit an alert to the Patient Monitor 605. The alert can include an identifier of the RFID tag. In another aspect of the disclosure, instead of converting the output of the comparator into a signal for transmission (such as a digital signal), a preset signal for the alert can be used (converted and transmitted).

Alternatively, the second set of switches $510_N$ can be omitted, and the voltage/current can be applied to the conductive elements 425 at the same time.

In another aspect of the disclosure, the memory can store a second set volume for the transmission of a secondary alert. This second set volume is associated with another given comparator. For example, the second set volume can be 600 ml which is associated with comparator $425_{12}$. The RFID Controller 400A will cause the A/D converter 420 to convert the output of the comparator into a digital signal if comparator $425_{12}$ (or a comparator associated with a volume above the same) indicated a difference and cause the transmitter 405 to transmit an alert to the Patient Monitor 605. In another aspect of the disclosure, instead of converting the output of the comparator into a signal for transmission (such as a digital signal), a second preset signal for the alert can be used (converted and transmitted), where the second preset signal is different from the first signal.

In another aspect of the disclosure, the RFID Controller 400A can store in the memory the comparator(s) that indicate a difference. Any subsequent polling from the RFID tag 30A from the Patient Monitor 605 can start the sequential switching from the lowest volume level that indicated a difference. This will reduce processing load on the RFID Controller 400A.

In another aspect of the disclosure, instead of transmitting an alert upon a first instance of the voltage (or current) being determined to be different from the respective reference value, an alert can be transmitted when at least a certain number of polling periods have occurred when the voltage (or current) is different. For example, the memory of the RFID Controller 400A can store at least one previous result(s) of the comparisons and the transmission threshold(s). If a transmission threshold is two polling periods, the RFID Controller 400A can cause the alert to be generated when the voltage (or current) from a respective comparator is determined to be different for two consecutive polling periods. Thus, the RFID Controller 400A can retrieve previous determination(s) from memory and the transmission threshold(s) and compare the previous determination(s) with a current determination.

In another aspect of the disclosure, instead of transmitting an alert upon a first instance of the voltage (or current) being determined to be different from the respective reference value, an alert can be transmitted based on looking at the difference between the values (voltage or current) from consecutive polling periods, e.g., the delta, without a separate reference value. A change in the values (voltage or current) indicates that the fluid level has reached the respective conductive element (whereas the period prior it did not).

In another aspect of the disclosure, instead of the RFID controller 400A determining whether an alert should be transmitted based on the respective output of the comparator $425_{1-N}$, the A/D converter 420 converts the output of each of the plurality of comparators $425_{1-N}$, for each instance of the polling, and the raw data is transmitted by the transmitter 405 for external evaluation.

If the Patient Monitor 605 receives an alert from the RFID tag 30A (via the RF reader), the Patient Monitor 605 sends an alert to the nurses station 610. The nurses station 610 can include a display and the alert can be displayed on the display. Additionally and/or alternatively, the nurses station 610 can include a speaker and an audible alert can be generated. In response to the alert, a nurse can change the fluid collection bag 1, if needed. Furthermore, the nurse can record the fluid level in a patient's file.

The patient monitor 605 will also poll the burette 1A having the RFID tag 30A. The RFID tag 30A in the burette 1A responds in the same way as described above and will not be described again in detail.

A memory is any piece of hardware that is capable of storing information, such as, for example without limitation, data, programs, instructions, program code, and/or other suitable information, either on a temporary basis and/or a permanent basis.

The terms "RFID Controller" as may be used in the present disclosure may include a variety of combinations of hardware including a control circuit, hardware and software, and storage devices. The "RFID Controller" may include a plurality of individual circuit components linked to perform collaboratively, or may include one or more stand-alone components.

The terminology used herein is for the purpose of describing particular embodiments only and is not intended to be limiting the scope of the disclosure and is not intended to be exhaustive. Many modifications and variations will be apparent to those of ordinary skill in the art without departing from the scope and spirit of the disclosure.

What is claimed is:

1. A fluid container comprising:
   a wall forming a volume for holding a fluid, the wall having a plurality of volume marking indicating a plurality of volume levels;
   a plurality of integral conductive elements, each disposed at a particular volume level, each of the conductive elements having a portion disposed within the volume and a portion external to the volume;
   a RFID tag; and
   an integral common conductive element having a portion disposed within the volume and a portion external to the volume, the common conductive element being connected to the RFID tag via a conductive wire, the conductive element being connected to the RFID tag via another conductive wire.

2. The fluid container of claim 1,
   wherein the conductive elements are attached to the wall, where the portion disposed within the volume is attached to an interior surface of the wall, the conductive elements extending through the wall and the portion external to the volume is external to the wall, wherein the another conductive wire is electrically coupled to the portion external to the volume and the RFID tag and extends along an exterior surface of the wall, wherein the RFID tag is disposed on the exterior surface of the wall; and wherein the common conductive elements are attached to the wall, where the portion of the common conductive elements disposed within the volume are attached to the interior surface of the wall, the common conductive elements extending through the wall and the portion external to the volume is external to the wall.

3. The fluid container of claim 2, wherein the plurality of volume markings, each respectively indicating a different specific volume and wherein each of the plurality of conductive elements being connected to the RFID tag via a respective conductive wire, the respective conductive wire is coupled to the portion of the conduct element external to the wall.

4. The fluid container of claim 3, wherein the plurality of conductive elements are vertically aligned.

5. The fluid container of claim 1, further comprising a cover configured to cover the plurality of integral conductive elements, the RFID tag, and the integral common conductive element.

6. The fluid container of claim 3, further comprising a cap having an inlet, the inlet configured to receive a fluid supply line and a controllable outlet for delivering fluid from the volume.

7. The fluid container of claim 6, wherein the fluid holding device is a burette.

8. The fluid container of claim 6, wherein the fluid supply line is an intracranial catheter.

9. A fluid container comprising:
a wall forming a volume for holding a fluid, the wall having a volume marking indicating a volume level;
a conductive element disposed at the volume level, the conductive element having a portion disposed within the volume and a portion external to the volume;
a RFID tag; and
a common conductive element having a portion disposed within the volume and a portion external to the volume, the common conductive element being connected to the RFID tag via a conductive wire, the conductive element being connected to the RFID tag via another conductive wire,
wherein the wall is formed from a first layer and a second layer, each of the first layer and a second layer have a first portion and a second portion, the first portion of each of the first layer and the second layer form the volume,
wherein the first layer is attached to the second layer at a seam to form the volume,
wherein the conductive element and the common conductive element is disposed along the seam such that a portion of the conductive element and the common conductive element is within the volume and a portion of the conductive element and the common conductive element is disposed between the second portion of the first layer and the second portion of the second layer and outside the volume,
wherein the conductive wire is coupled to the portion of the conductive element between the second portion of the first layer and the second portion of the second layer and wherein the another conductive wire is coupled to the portion of the common conductive element disposed between the second portion of the first layer and the second portion of the second layer,
wherein the RFID tag is disposed between the second portion of the first layer and the second portion of the second layer, and
wherein the conductive wire and the another conductive wire connects the portion of the common conductive element and the conductive element, respectively and the RFID tag, the conductive element and the another conductive element disposed between the second portion of the first layer and the second portion of the second layer.

10. The fluid container of claim 9, wherein the wall has a plurality of volume markings, each respectively indicating a different specific volume and wherein the fluid container has a plurality of conductive elements respectively disposed at each of the different specific volumes, each of the plurality of conductive elements being disposed along the seam such that a portion is within the volume and a portion is disposed between the second portion of the first layer and the second portion of the second layer, each of the plurality of conductive elements being connected to the RFID tag via a respective conductive wire, the respective conductive wire is coupled to the portion of the conductive element between the first layer and the second layer.

11. The fluid container of claim 10, further comprising an inlet disposed between the first portion of the first layer and the first portion of the second layer, the inlet being sealed therebetween, the inlet configured to receive a fluid.

12. A fluid detection system comprising:
a fluid container comprising:
a wall, at least a portion of the wall defining a volume to hold a fluid, the wall having a volume marking indicating a volume level,
a RFID tag attached to the wall, and comprising a memory;
a plurality of conductive elements, each disposed at a particular volume level, each of the conductive elements having a portion disposed within the volume and a portion external to the volume;
a common conductive element having a portion disposed within the volume and a portion external to the volume, the common conductive element and the conductive element being connected to the RFID tag via respective conductive wires; and
a patient site monitor having a RF Reader, the RF Reader being configured to interrogate the RFID tag at a preset interval by transmitting a signal,
wherein when the RFID tag receives the signal, the RFID tag supplies a predetermined current to the conductive element and the common conductive element and detects a voltage,
wherein the RFID tag is configured to generate an alert based on the voltage responsive to the signal, and
wherein the RFID tag memory stores the detected voltage for at least the preset interval and the RFID tag is configured to generate an alert when the detected voltage for a current period is different from the stored detected voltage.

13. The fluid detection system of claim 12, further comprising:
a nursing station, wherein when the alert is received by the RF Reader in the patient site monitor, the patient site monitor is configured to transmit a second alert to the nursing station.

14. The fluid detection system of claim 12, wherein the RFID tag comprises a controller and a comparator, wherein the comparator compares the detected voltage to confirm a fluid level, and wherein the RFID tag is configured to generate the alert when the detected voltage is different from the predetermined voltage.

15. The fluid detection system of claim 12, wherein the RFID tag comprises a controller and a comparator,
wherein the comparator compares the detected voltage with a predetermined voltage; and
wherein the RFID tag is configured to generate the alert when the detected voltage is different from the predetermined voltage.

16. The fluid detection system of claim 12, wherein the plurality of volume markings, each respectively indicating a different specific volume and wherein each of the plurality of conductive elements being connected to the RFID tag via a respective conductive wire, the respective conductive wire is coupled to the portion of each of the conductive elements external to the volume; and
wherein when the RFID tag receives the signal, the RFID tag sequentially supplies a predetermined current to a respective conductive element of the plurality of conductive elements and the common conductive element and sequentially detects a voltage between the respective conductive element and the common conductive element, wherein the RFID tag is configured to generate an alert based on the detected voltages between each of the respective conductive elements and the common conductive element, responsive to the signal.

17. The fluid detection system of claim 16, wherein the RFID tag comprises a controller and at least one comparator,
wherein the at least one comparator compares the detected voltages between each of the respective conductive elements and the common conductive element with respective predetermined voltages to determine a fluid level, and wherein the RFID tag is configured to generate the alert when the determined fluid level is above a first preset fluid level.

18. The fluid detection system of claim 17, wherein RFID tag is configured to generate another alert when the determined fluid level is above a second preset fluid level.

19. The fluid detection system of claim 12, wherein the RFID tag is a passive tag.

20. The fluid detection system of claim 12, wherein the conductive element is disposed at a maximum fill level for the fluid container.

21. The fluid detection system of claim 13, wherein the patient site monitor further comprises a wireless adapter and the second alert is transmitted to the nursing station via the wireless adapter.

* * * * *